(12) United States Patent
Beller

(10) Patent No.: US 10,688,259 B2
(45) Date of Patent: Jun. 23, 2020

(54) INHALATION DEVICE, USE THEREOF, AND INHALATION KIT

(71) Applicant: Klaus-Dieter Beller, Kenzingen (DE)

(72) Inventor: Klaus-Dieter Beller, Kenzingen (DE)

( * ) Notice: Subject to any disclaimer, the term of this patent is extended or adjusted under 35 U.S.C. 154(b) by 362 days.

(21) Appl. No.: 15/534,501

(22) PCT Filed: Dec. 9, 2015

(86) PCT No.: PCT/EP2015/002483
§ 371 (c)(1),
(2) Date: Jun. 9, 2017

(87) PCT Pub. No.: WO2016/091386
PCT Pub. Date: Jun. 16, 2016

(65) Prior Publication Data
US 2017/0326312 A1  Nov. 16, 2017

(30) Foreign Application Priority Data
Dec. 9, 2014 (DE) .................. 10 2014 018 085

(51) Int. Cl.
*A61M 15/00* (2006.01)
*A61M 15/08* (2006.01)

(52) U.S. Cl.
CPC ...... *A61M 15/0036* (2014.02); *A61M 15/003* (2014.02); *A61M 15/0028* (2013.01);
(Continued)

(58) Field of Classification Search
CPC ............ A61M 15/003; A61M 15/0031; A61M 15/0033; A61M 15/0036; A61M 15/0035;
(Continued)

(56) References Cited

U.S. PATENT DOCUMENTS 5,070,870 A * 12/1991 Pearce .............. A61M 15/0028
128/203.12
5,819,730 A * 10/1998 Stone ................ A61M 15/0028
128/203.21
(Continued)

FOREIGN PATENT DOCUMENTS

DE  10 2005 043 449   8/2006
DE  10 2008 060 675   6/2010
(Continued)

*Primary Examiner* — Kendra D Carter
*Assistant Examiner* — Elliot S Ruddie
(74) *Attorney, Agent, or Firm* — Gudrun E. Huckett

(57) ABSTRACT

The present invention relates to an inhalation device (1), to the use thereof, and to a kit comprising the inhalation device. The inhalation device (1) has an air inlet (14), an air outlet (15) designed as a mouthpiece or nosepiece, and a recess (17) which is designed to receive a container (2) with an inhalable substance. An air duct (L) extends from the air inlet (14) through the recess (17) to the air outlet (15). Moreover, the inhalation device (1) has at least one hollow mandrel (16, 16') which protrudes into the recess (17) and from which at least one air delivery line (14', 14") extends to the air inlet (14) or at least one air outlet line (15') extends to the air outlet (15). The inhalation device (1) is characterized in that the inhalation device (1) has two limbs (11, 12), each with a work end (11', 12') and with an actuation end (11", 12"), wherein the limbs (11, 12) are connected by means of a joint (13) which lies between the work ends (11', 12') and the actuation ends (11", 12"). Furthermore, the recess (17) is defined between the mutually facing sides of both limbs (11, 12) at the work ends (11', 12'), wherein the at least one hollow mandrel (16, 16') is arranged inside the recess (17) on one of the mutually facing sides of both limbs (11, 12). The air inlet (14) and the air outlet (15) are arranged at the work end (11', 12') on a side, directed away from the recess (17), of at least one of the limbs (11, 12).

18 Claims, 10 Drawing Sheets

Figure 1:
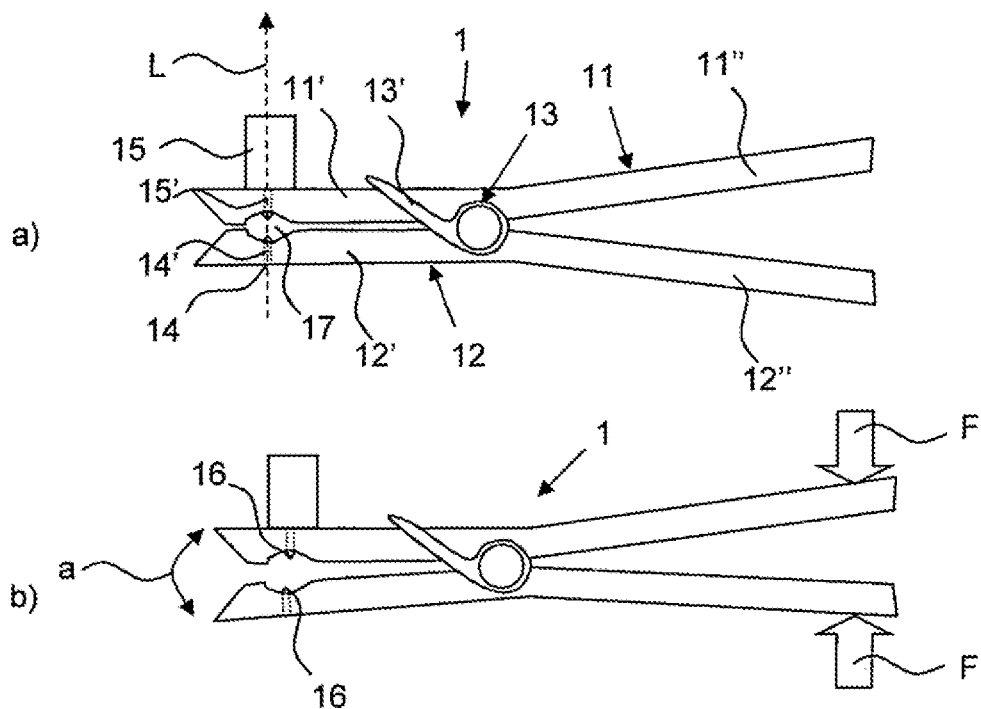

(52) U.S. Cl.
CPC .... *A61M 15/0035* (2014.02); *A61M 15/0041* (2014.02); *A61M 15/08* (2013.01); *A61M 2202/064* (2013.01)

(58) Field of Classification Search
CPC ............ A61M 15/0038; A61M 15/004; A61M 15/0041; A61M 15/0045; A61M 15/0061; A61M 15/0063; A61M 15/0028; A61M 15/08; A61M 2202/06; A61M 2202/064
USPC .................................................... 128/203.21
See application file for complete search history.

(56) References Cited

U.S. PATENT DOCUMENTS

| | | | |
|---|---|---|---|
| 2008/0314384 A1* | 12/2008 | Harris | A61M 15/0028 128/203.15 |
| 2009/0314293 A1* | 12/2009 | Djupesland | A61M 11/00 128/203.18 |
| 2010/0000531 A1* | 1/2010 | Smith | A61M 15/0028 128/203.15 |
| 2011/0253783 A1 | 10/2011 | Baque et al. | |
| 2013/0074841 A1* | 3/2013 | Von Schuckmann | A61M 15/0028 128/203.15 |
| 2013/0158474 A1* | 6/2013 | Sullivan | A61M 11/06 604/68 |
| 2015/0028219 A1 | 1/2015 | Baque et al. | |
| 2015/0068955 A1 | 3/2015 | Baque et al. | |
| 2015/0217539 A1 | 8/2015 | Baque et al. | |

FOREIGN PATENT DOCUMENTS

| | | |
|---|---|---|
| DE | 10 2012 003 519 | 8/2013 |
| DE | 10 2012 005 542 | 9/2013 |
| DE | 10 2012 017 710 | 3/2014 |
| EP | 1 762 265 | 3/2007 |

* cited by examiner a)

b)

a)

b)

a)

b)

INHALATION DEVICE, USE THEREOF, AND INHALATION KIT

The invention relates to an inhalation device by means of which an inhalable substance present in a container in the device can be inhaled. Furthermore, the invention relates to an inhalation kit consisting of inhalation device and container and to use of the inhalation device.

In the case of conventional inhalers which are used with a container containing a substance as powder dose for a single application (single dose), such as a capsule or a blister for example, a fixed combination of inhaler and container is stipulated: in this case, only a certain container type can be used with the available inhaler. In the event of a defect or loss of the inhaler, the user can no longer use the containers that are still available.

An example of a single-dose inhaler is disclosed in DE 10 2005 043 449 B3. It describes an inhalation device having a tubular housing which is axially divided into two housing parts which delimit an axial through-channel and of which one is designed as a mouthpiece or nosepiece and the other as an air inlet. Fitted together, the two housing parts form a chamber for accommodating a capsule containing an inhalable powder. For the perforation of the capsule inserted into the chamber, each housing part has a pyramid-shaped spike protruding into the chamber, and so the capsule is perforated at opposite ends and a passage communicating with the through-channel is generated by the capsule when the housing parts are axially moved toward one another.

Proceeding from this prior art, it is an object of the present invention to provide an easily and cost-effectively producible inhalation device for single-dose containers with a broad usage spectrum, which is easy to use.

This object is achieved by an inhalation device having the features of claim 1.

Preferred embodiments are stated in the dependent claims.

Furthermore, use of the inhalation device having the features of claim 10 is disclosed.

The further object of providing an easily usable and cost-effectively producible inhalation kit is achieved by the inhalation kit having the features of independent claim 11.

Like conventional inhalation devices, an inhalation device according to the invention comprises an air inlet, an air outlet designed as a mouthpiece or nosepiece, and a recess designed to accommodate a container containing an inhalable substance. The inhalable substance can, for example, be an active-ingredient-containing powder or a vaporizable aroma preparation. In the inhalation device, an air channel stretches from the air inlet to the air outlet through the recess, into which one or more hollow spikes protrude. Depending on the number of hollow spikes, an air feed line stretches from the hollow spike in question to the air inlet or an air outlet line stretches from the hollow spike in question to the air outlet. According to the invention, the inhalation device comprises, similarly to pliers or a clothespin, two arms having in each case an action end and an actuation end, the arms being joined by means of a joint lying between the action ends and the actuation ends. The recess designed to accommodate the container is defined between the mutually facing sides of the two arms at the action ends, the hollow spike(s) being arranged inside the recess on one of the mutually facing sides of the two arms. Depending on the arrangement of the hollow spikes, the air inlet and the air outlet are arranged at the action end on a side of at least one of the arms, which side is facing away from the recess. Advantageously, the inhalation device according to the invention can be extremely small in dimension and be of a size similar to that of a pocket lighter. In addition, an inhalation device according to the invention has a broad usage spectrum, since it is possible to use various containers, for example both blisters and capsules.

In different embodiments of the inhalation device according to the invention, the action ends can—depending on the design of the joint—be opened or closed by actuation of the arms at the actuation ends; however, the joint can be preferably designed such that an open position of the action ends is provided upon the actuation ends being brought together.

Furthermore, an inhalation device according to the invention can comprise a reset device which is in operative connection with the two arms in order to provide a closed position of the action ends, i.e., the reset force provided by the reset device counteracts the opening of the action ends or assists the closing of the action ends.

Preferably, the joint can comprise the reset device, meaning that the inhalation device is constructed from as few components as possible. In this connection, an arm spring can simultaneously serve as joint and reset device, or these functions can, in a particularly preferred embodiment, be assumed by a film hinge which—when the inhalation device is made of plastic—can be integrally joined to the arms.

However, it is also possible to provide a reset device which is separate from the joint and which can, for example, be an elastic strap arranged around the action ends or be a spring, preferably coil spring, arranged between the arms at the actuation ends.

A further embodiment of an inhalation device according to the invention comprises a single hollow spike provided with an integrated bypass air supply line. Another embodiment of an inhalation device according to the invention provides at least two hollow spikes, of which at least one is assigned to the air inlet via the at least one air feed line and at least one is assigned to the air outlet via the at least one air outlet line. Multiple air feed lines or air outlet lines can be assigned to each hollow spike. The two or more hollow spikes can be arranged on one of the arms, meaning that air inlet and air outlet are situated on the same side on the same arm. Alternatively, at least one of the two or more hollow spikes can be arranged on each arm, meaning that air inlet and air outlet point in opposite directions on both arms. In this connection, the hollow spikes can either be arranged opposite one another or be arranged offset with respect to one another.

The inhalation device can cost-effectively be made partially or preferably entirely and as one piece from plastic in an injection-molding process. Optionally, the hollow spike(s) can be composed of metal instead of plastic and be integrated, effectively as an insert, into the injection-molded inhalation device.

Thus, the inhalation device cost-effectively produced in a plastics injection-molding process can advantageously also be envisaged as a replacement inhaler and is also suitable for sale or distribution in Third World countries.

Each hollow spike can be pyramid-shaped, it being possible to give preference to pyramids having a triangular base area, since the edges here exhibit an optimal cutting result in the penetration of the container wall. If the inhalation device comprises more than one hollow spike, these can also be designed differently.

To improve the air flow conditions through the container, the air inlet and/or the air feed line can comprise aerodynamic air diversion elements which, for example, rotate or twist the air stream. Preferably, said air diversion elements are created integrally with the inhalation device and not as separate elements, especially when the inhalation device is made in a plastics injection-molding process.

In the case of a pyramid-shaped hollow spike, an air feed line can be provided on each side. To twist the sucked-in air stream, the air feed lines can be arranged asymmetrically, i.e., in the case of an even three-sided pyramid not at an angle of 120°. Alternatively or additionally, the air feed lines can have different diameters in order to generate a desired vortex at the inlet into the container.

Furthermore, the inhalation device can, especially since it is also intended for use with containers containing a vaporizable substance, comprise a heating device containing a heating element which protrudes into the recess or is arranged in or along the air inlet and/or the air feed line. Such a heating device can be operated using an energy source such as a battery or an accumulator, for which it is possible to provide in one of the arms an accommodating compartment having corresponding electrical contacts that are connected to the heating device.

To improve the disagglomeration of the powder to be inhaled, the inhalation device can comprise a disagglomeration attachment which is arranged on the air outlet in a detachable or nondetachable manner and has a disagglomeration structure which can stretch across the entire cross section of the air outlet.

The disagglomeration structure can be latticed and thus additionally serve to collect film fragments, it being possible for the latticed disagglomeration structure to be planar or curved. The curvature direction, which can be concave or convex, and also the mesh size of the latticed disagglomeration structure can be selected depending on the nature of the powder to be inhaled using the inhalation device.

According to the invention, said inhalation device can be used for perforating a container containing an inhalable substance and for providing the substance for inhalation.

An inhalation kit according to the invention comprises an inhalation device according to the invention and at least one container containing an inhalable substance.

The container can comprise a narrowing which, upon arrangement of the container in the recess of the inhalation device, be arranged between the air feed line and the air outlet line or correspondingly between multiple air feed lines and air outlet lines and ensure a quickening of the air stream and, as a result, an improved powder entrainment and disagglomeration.

Further embodiments and also some of the advantages associated with these and further embodiments will become clear and more easily understandable through the following detailed description with reference to the accompanying figures. Items or parts thereof which are essentially identical or similar may be provided with the same reference signs. The figures are merely schematic representations of exemplary embodiments of the invention.

Figure 2:
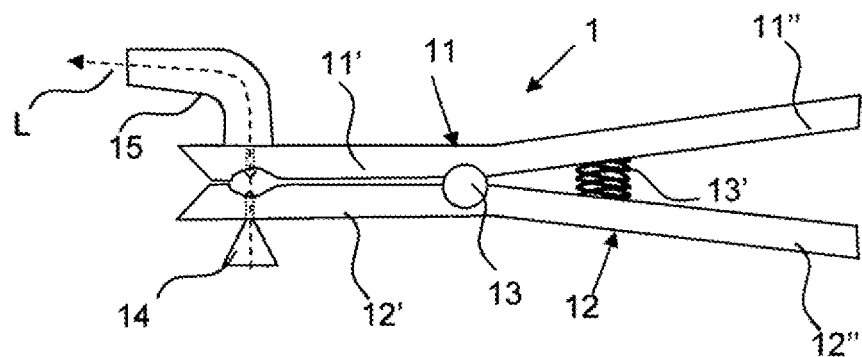
Figure 3:
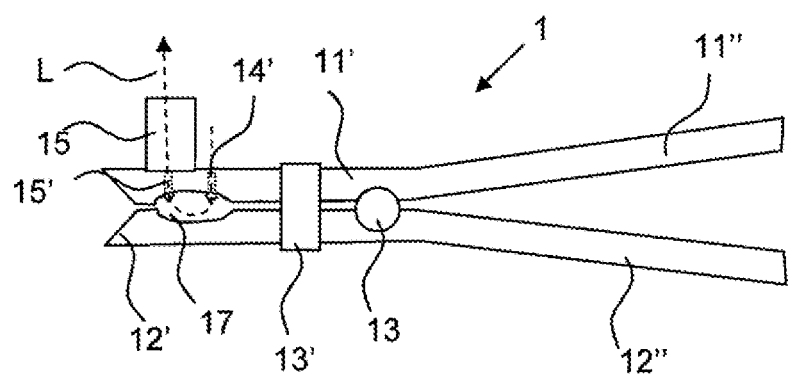
Figure 4:
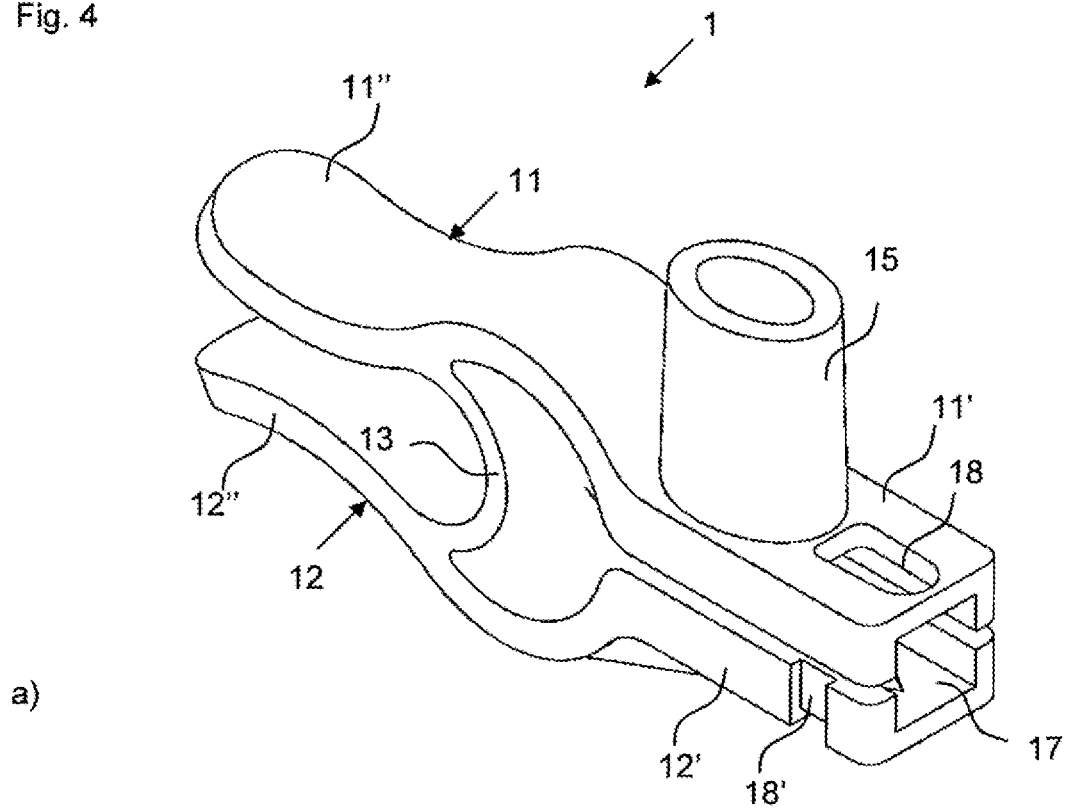
Figure 4:
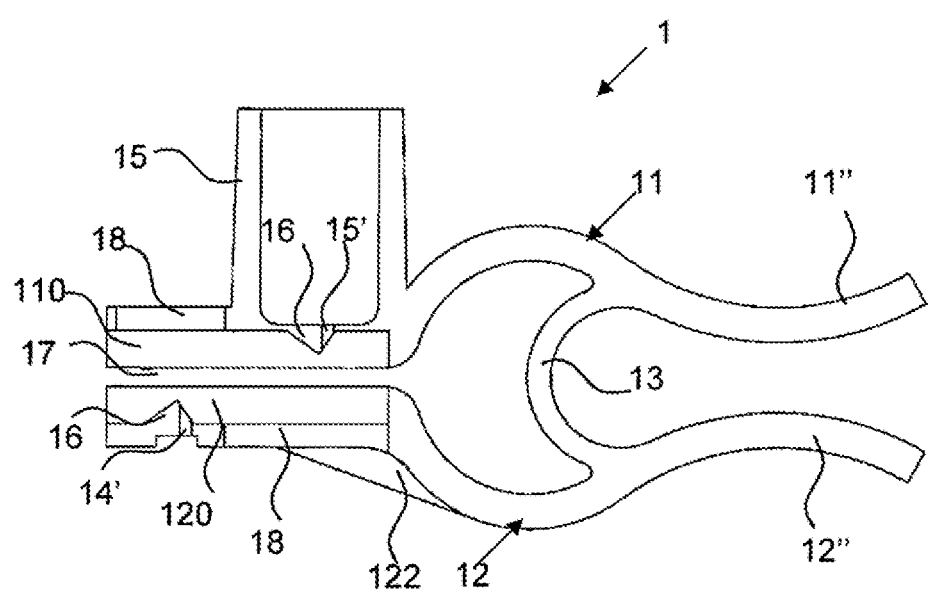
Figure 4:
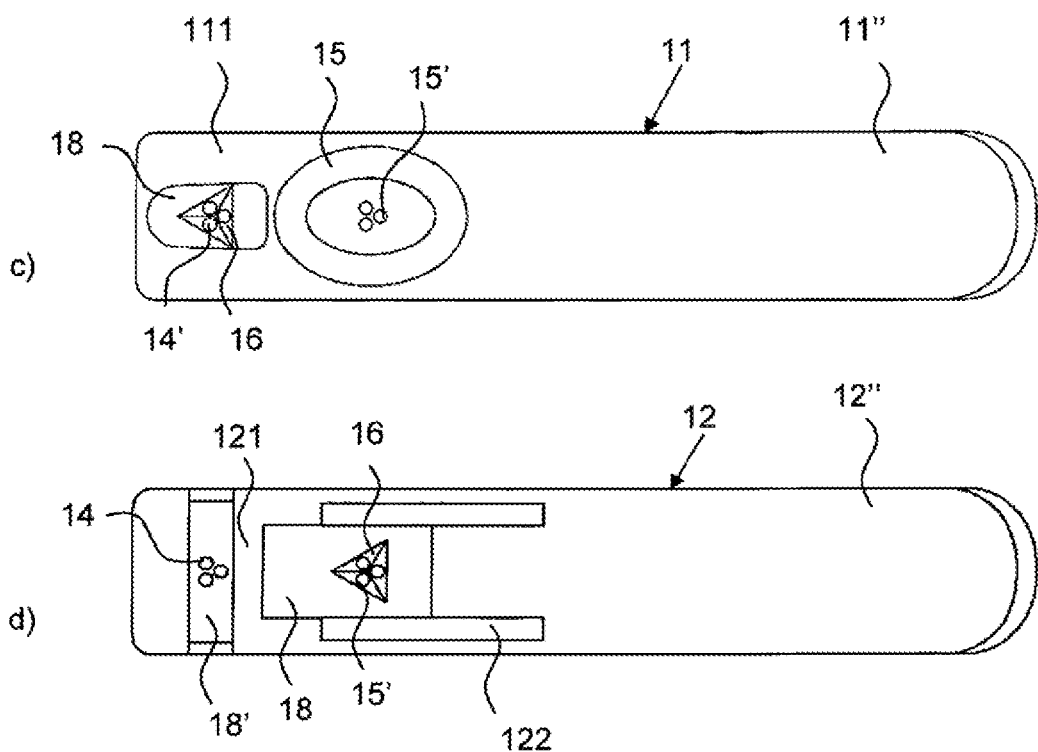
Figure 4:
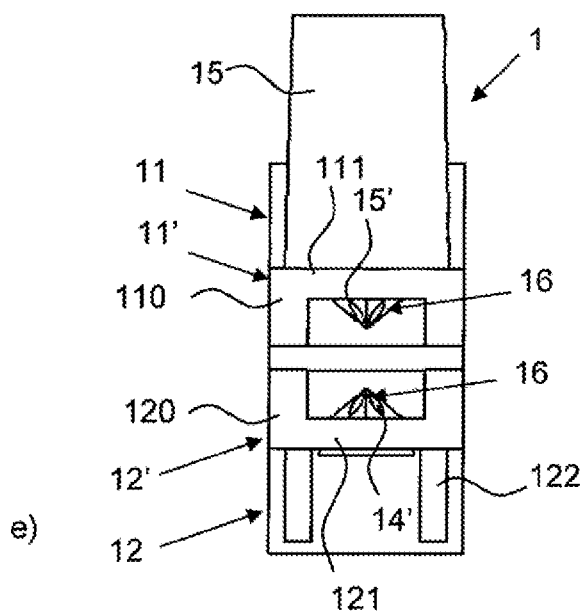
Figure 5:
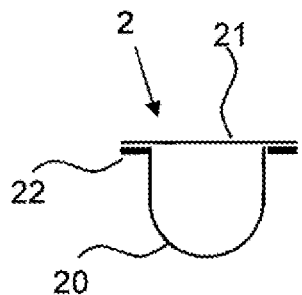
Figure 6:
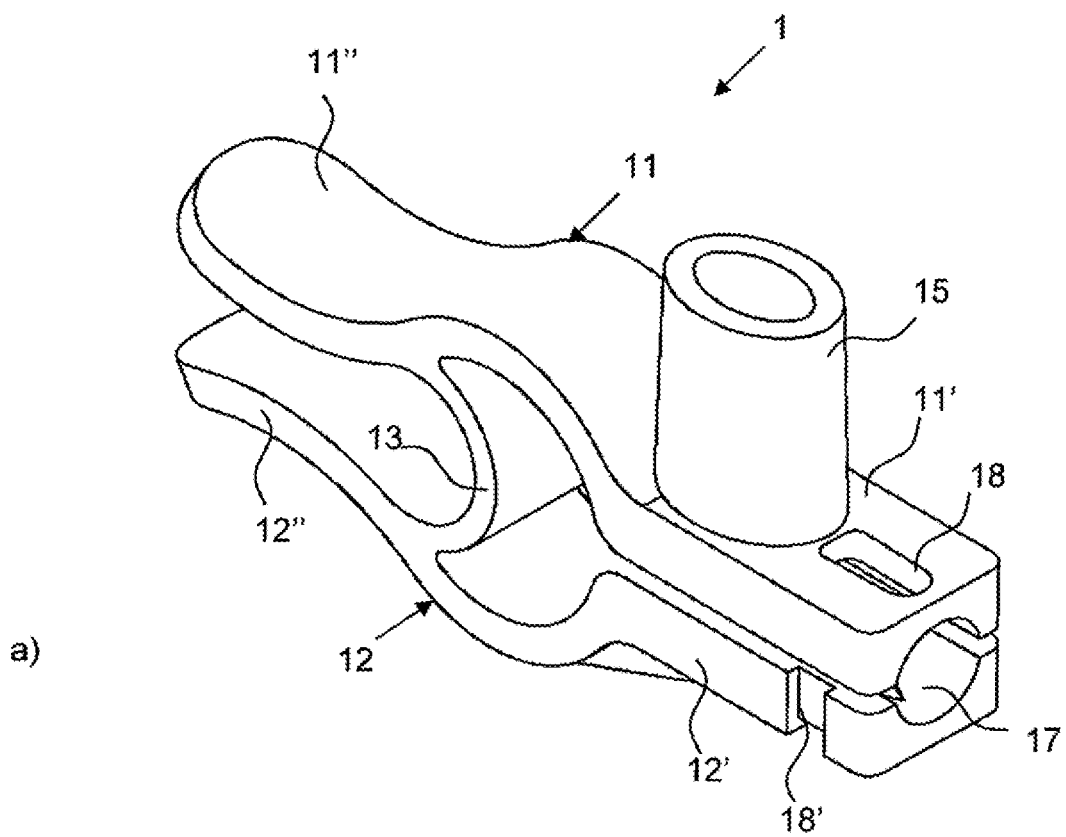
Figure 6:
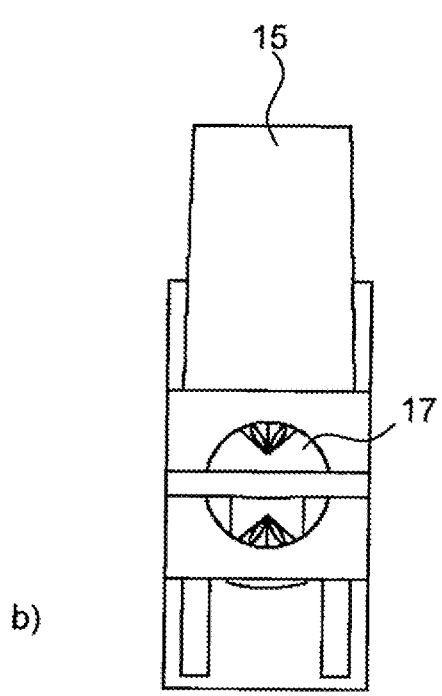
Figure 7:
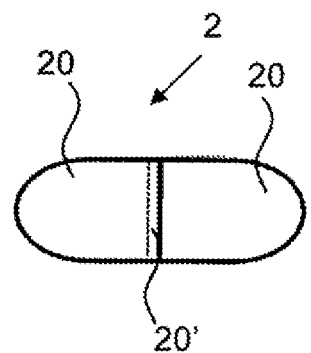
Figure 8:
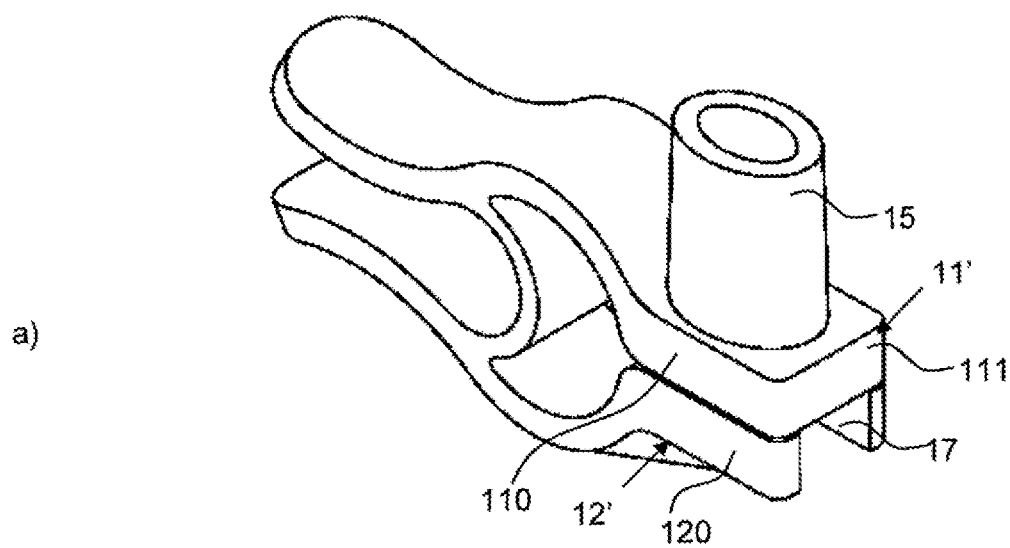
Figure 8:
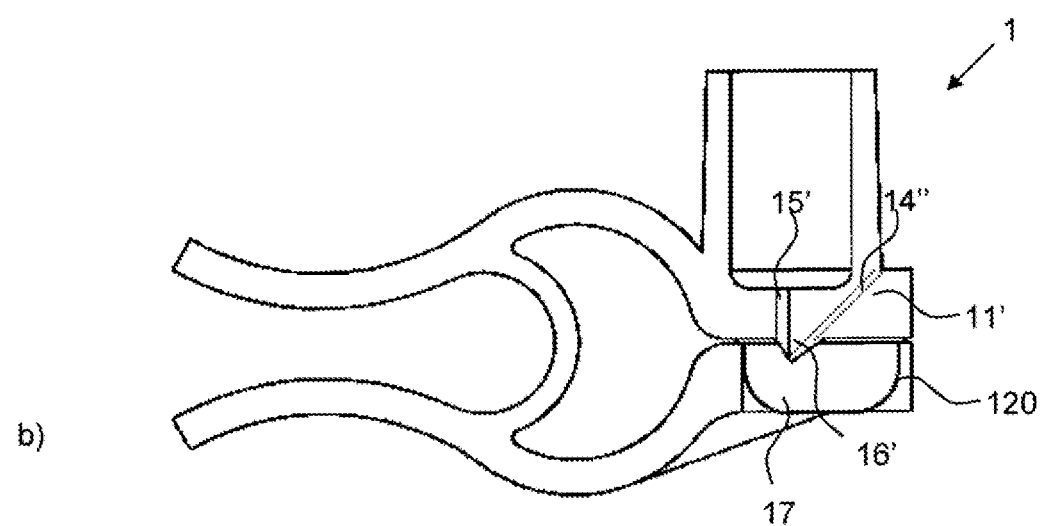
Figure 9:
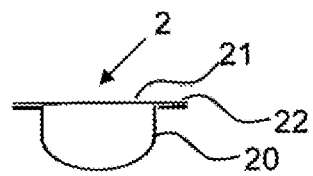
Figure 10:
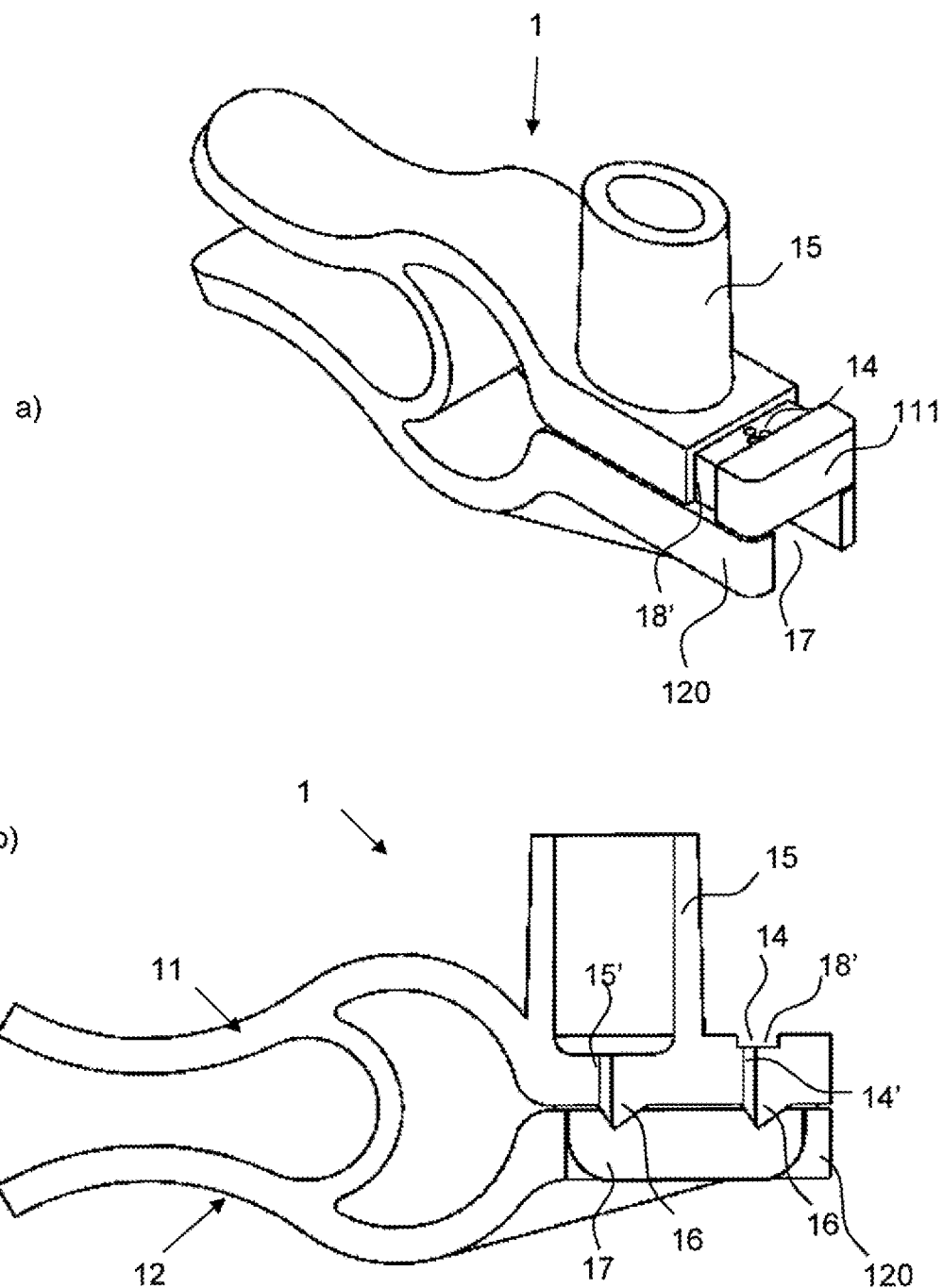
Figure 10:
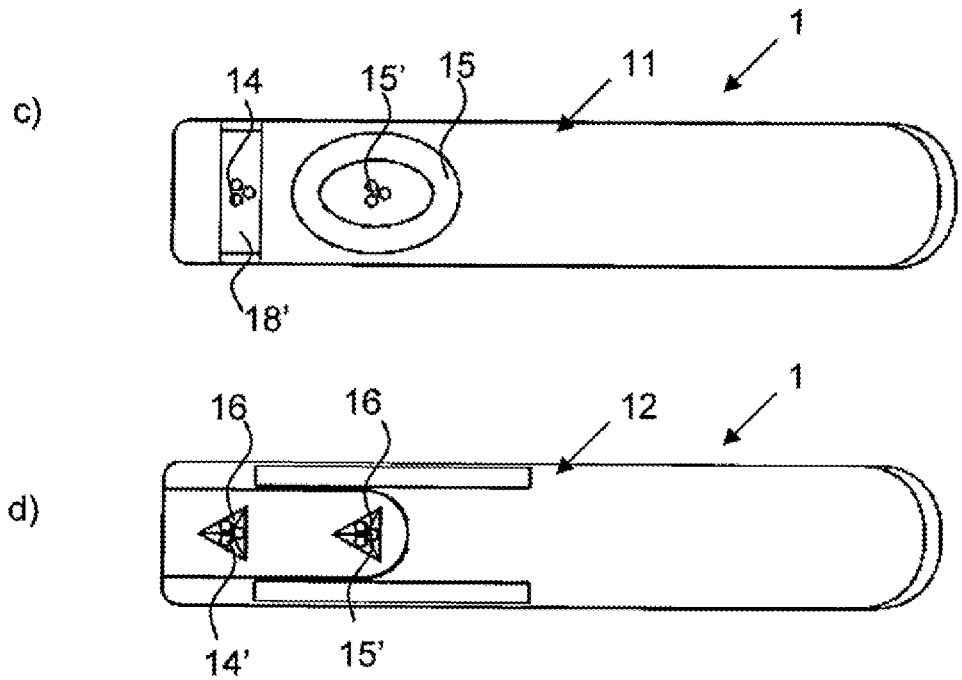
Figure 11:
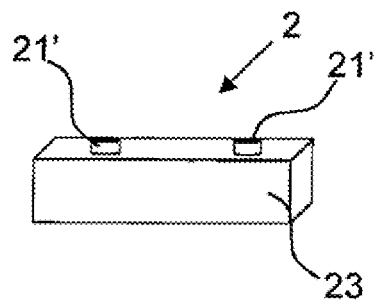
Figure 12:
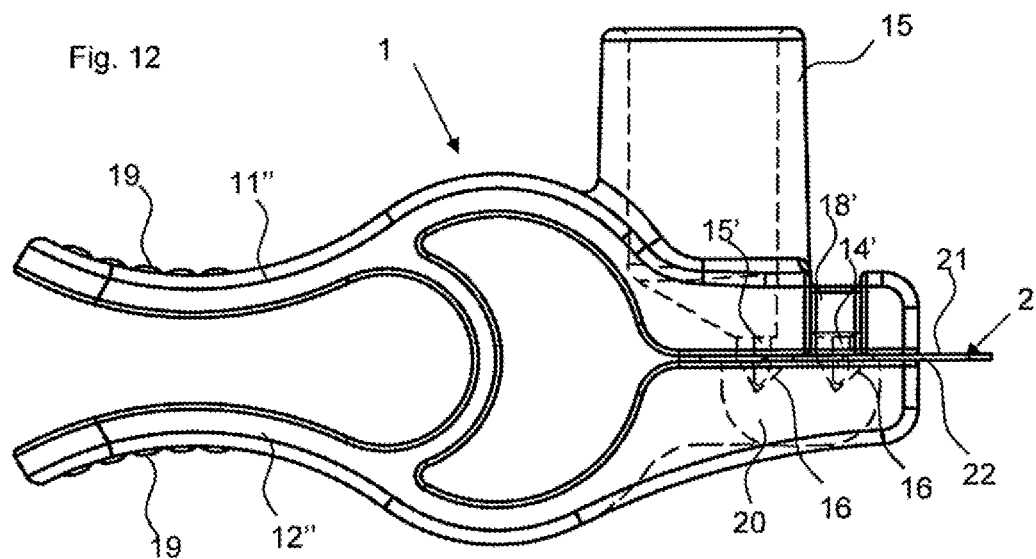
Figure 13:
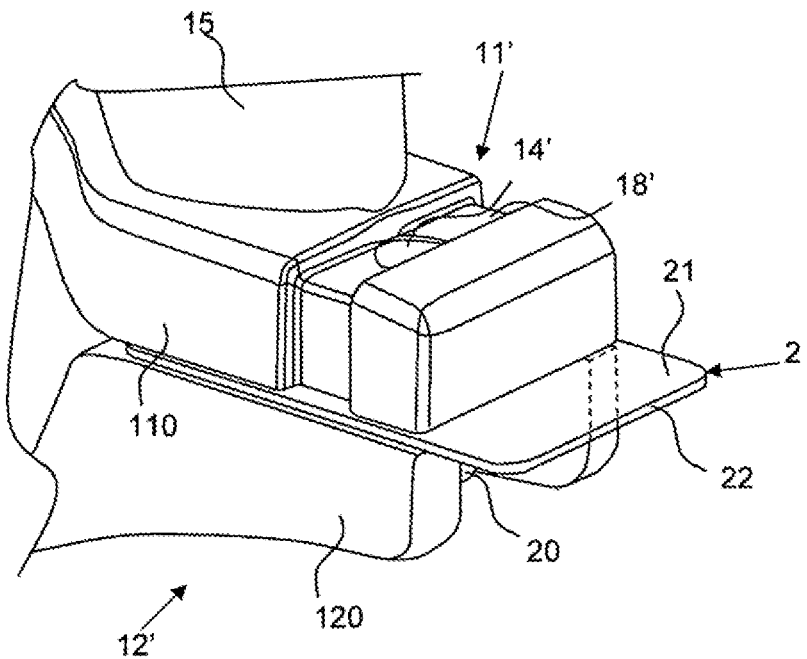
Figure 14:
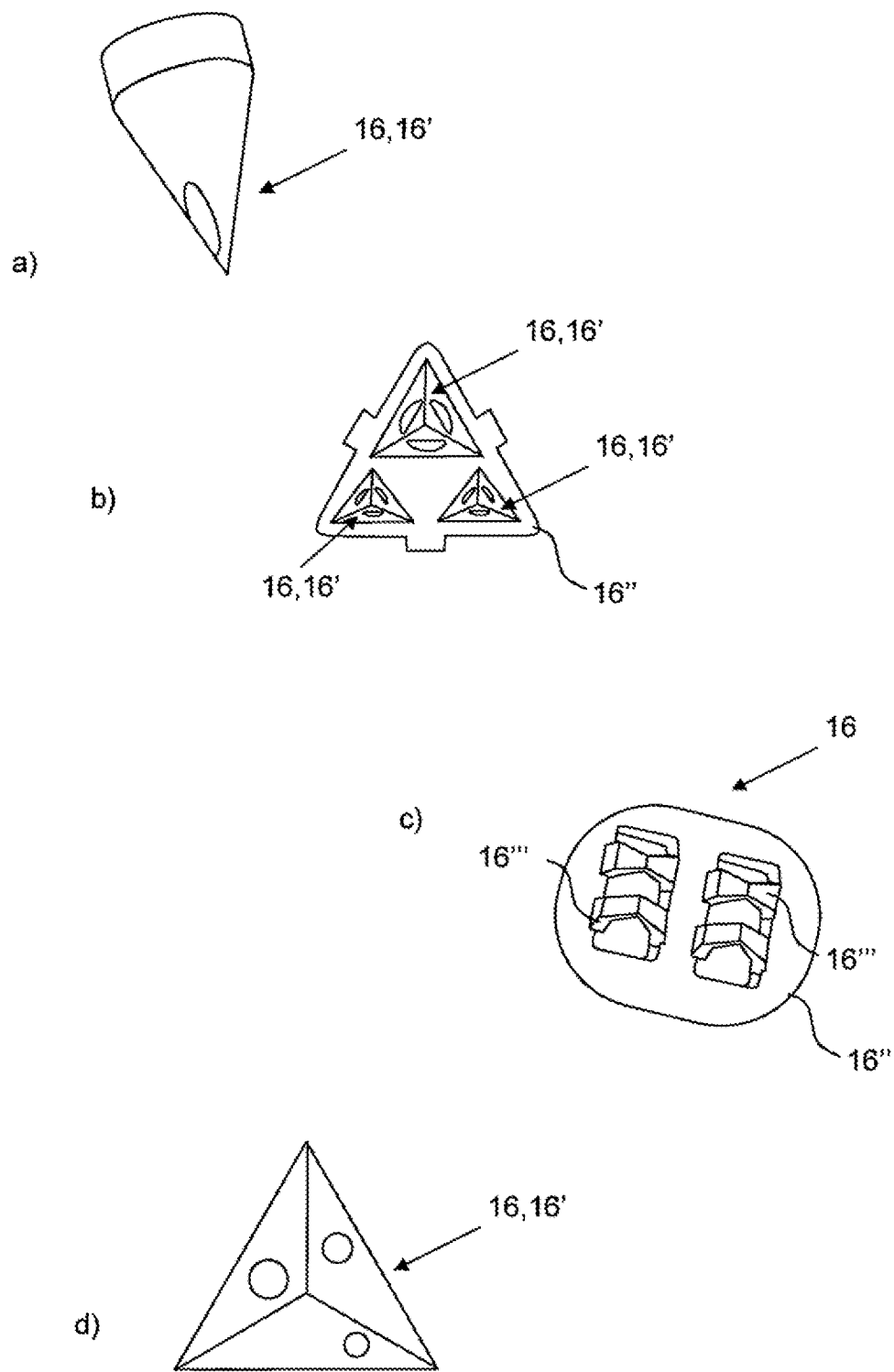
Figure 15:
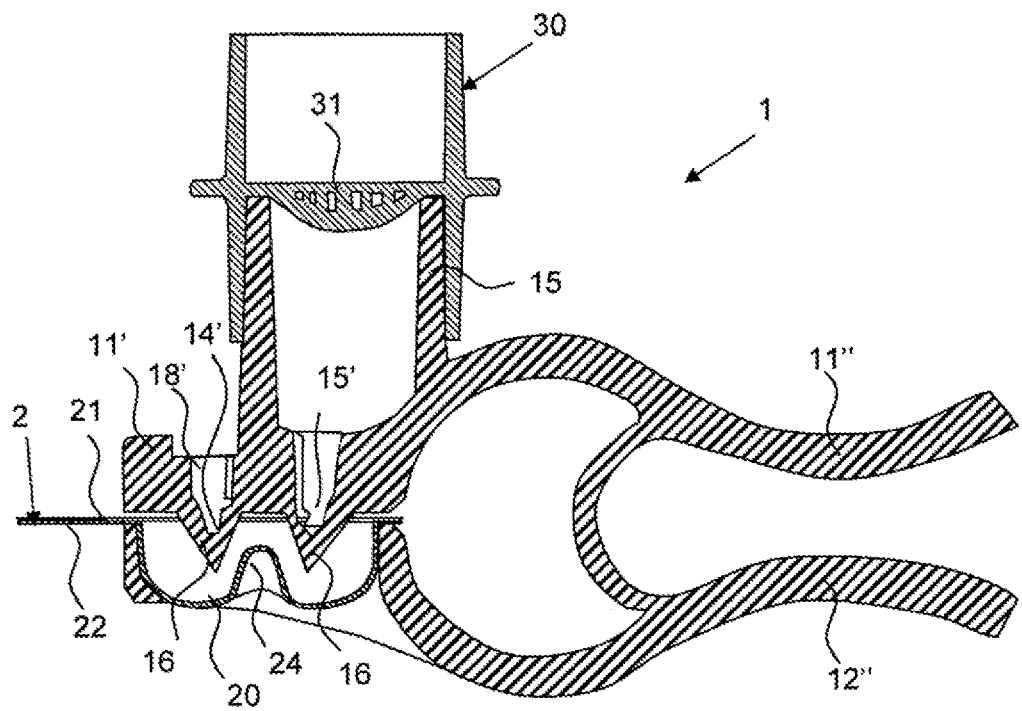
Figure 16:
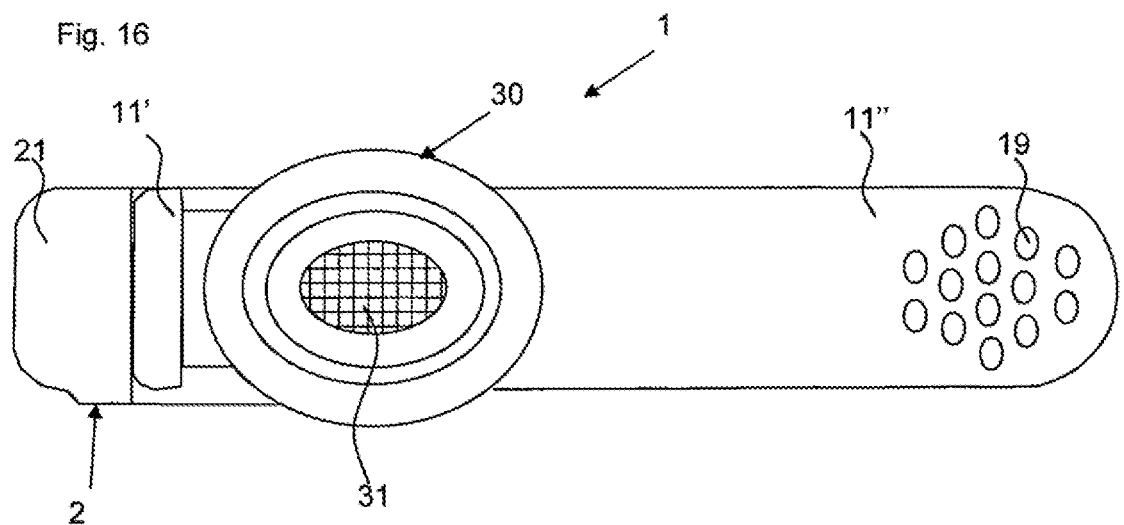

In the figures:

FIG. 1 shows a schematic side view of an inhalation device according to the invention a) with indicated air flow channel and b) in the open state, FIG. 2 shows a schematic side view of an alternative inhalation device according to the invention, FIG. 3 shows a schematic side view of a further alternative inhalation device according to the invention, FIG. 4 shows a one-piece inhalation device according to the invention in a) perspective view, b) longitudinal sectional view, c) top view, d) bottom view and e) front view, FIG. 5 shows a powder or aroma container suitable for use with the inhalation device from FIG. 4, FIG. 6 shows a one-piece inhalation device according to the invention having an alternatively designed accommodation area/cavity in a) perspective view and b) front view, FIG. 7 shows a powder or aroma container suitable for use with the inhalation device from FIG. 6, FIG. 8 shows a one-piece inhalation device according to the invention having a single hollow spike in a) perspective view, b) longitudinal sectional view, FIG. 9 shows a powder or aroma container suitable for use with the inhalation device from FIG. 8, FIG. 10 shows a one-piece inhalation device according to the invention having two hollow spikes on one arm in a) perspective view, b) longitudinal sectional view, c) top view and d) bottom view, FIG. 11 shows a powder or aroma container suitable for use with the inhalation device from FIG. 10, FIG. 12 shows a side view of a one-piece inhalation device having two hollow spikes on one arm with accommodated container, FIG. 13 shows a detailed perspective view of the inhalation device from FIG. 12 with accommodated container, FIG. 14 shows a) to d) different hollow spikes, FIG. 15 shows a lateral sectional view through an inhalation device having a disagglomeration structure at the air outlet, FIG. 16 shows a top view of the inhalation device from FIG. 15.

The device according to the invention concerns an inhalation device for the nasal and/or inhalation-based administration of common containers such as capsules, individual blisters or cartridges containing an inhalable substance. This can be a pulverulent or vaporizing or vaporizable inhalable active ingredient or aromatic substance.

So that an inhalation device according to the invention can be used as replacement inhaler or emergency inhaler and be sold or distributed in Third World countries, where patients or charities cannot afford relatively expensive inhalers, the main focus is on cost-effective production, broad usage spectrum and simple handling. Therefore, this simple inhaler is designed such that various powder or aroma containers—both blisters and capsules, etc.—can be used therewith; however, variants of the inhalation device according to the invention can also be designed such that a combination with a certain powder or aroma container is particularly appropriate.

Similarly to pliers, an inhalation device 1 according to the invention, as shown in FIGS. 1 to 4, 6, 8, 10, 12, is constructed from two arms 11, 12 joined by means of a joint 13. The arm ends on the one side of the joint 13 have, as action ends 11', 12', action sites such as needles, spikes 16, 16' or blades and a holding or accommodating device 17 for a container 2 (see FIGS. 5, 7, 9, 12, 13), whereas the arms ends on the other side of the joint 13 are designed as handles or actuation ends 11", 12" for opening or closing the inhalation device 1 at the action ends 11', 12'. The action ends 11', 12' are opened in order to insert or remove a container 2; upon closure of the action ends 11', 12', the inserted container 2 is opened or perforated by the particular opening means—needles, (hollow) spikes 16, 16' or blades. When the action ends 11', 12' are closed, the inhalation device 1 containing the inserted container 2 is ready for use.

Depending on the design of arms and joint, the actuation movement at the actuation ends can be in the same direction as or in the opposite direction to the movement at the action ends. In the same direction means that the actuation ends being brought together brings about a closure of the action ends and that the actuation ends being moved apart brings about an opening of the action ends. In the case of a mode of operation in the opposite direction (as shown in the figures), the actuation ends 11", 12" being brought together brings about an opening of the action ends 11', 12' and vice versa. In general, all joints which are also known as plier joints are possible: a simple applied scissors articulation, in which the arms are put on top of one another and joined with a pivot bolt, a pushed-through scissors articulation, in which one arm is guided through an opening in the other arm, or an elastic connection of both arms that acts in an articulated manner.

In this connection, it can be envisaged that the handles or actuation ends as lever arms (force arms) are longer than the action ends (load arms), and so it is possible to achieve a more favorable transmission ratio between the force to be applied at the actuation ends and the opening path of the action ends.

In general, an actuation at the actuation ends may be necessary for both opening and closing the action ends; however, an inhalation device according to the invention will preferably comprise a reset device, which provides a pretension for closed action ends. As sketched in FIG. 1*b*, in order to transfer the action ends 11', 12' to the open position (indicated by double arrow a) of such an inhalation device 1, said pretension must be overcome by application of the force at the actuation ends 11", 12" (indicated by the block arrows F); however, after insertion of the container, the action ends 11', 12' automatically close (go to the closed position) when force is no longer exerted on the actuation ends, and the inhalation device 1 thus becomes ready for use as a result of the perforation of the container taking place at the same time, as depicted in FIG. 1*a*, though without container.

The dashed arrow L in FIGS. 1*a*, 2 and 3 indicates the path of an air flow through the inhalation device 1 when a container (not depicted) is accommodated in the recess 17 and perforated by the hollow spikes 16.

The air flow L is generated by an inhalation performed by a user at the air outlet 15 formed as a mouthpiece. In general, the air outlet 15, as indicated in FIG. 2, can also be formed as a nose nozzle. When using the inhalation device 1, ambient air flows through an air inlet 14, which can, as in FIG. 2, also be formed as an inlet funnel or similar, through an air feed line 14' to a first hollow spike 16, which protrudes into the recess 17 in which the container (not depicted) is accommodated and at the same time penetrates a wall of said container. The air flow L passes through the container, carries off the substance present, i.e., a powder or vaporized aromas, while doing so and exits at the second hollow spike 16, from which the air outlet line 15' stretches to the air outlet 15. The air inlet 14 or the air feed line 14' can contain aerodynamic air diversion elements (not depicted in the figures) which rotate or twist the drawn-in air stream, wherein the air diversion element(s) are not a separate component, but are created integrally with the corresponding arm, preferably in an injection-molding process.

The air inlet 14 and air outlet 15 can, as shown in FIGS. 1 and 2, be distributed on both arms 11, 12 or, as depicted in FIG. 3, be arranged on one arm 11. An arrangement of the hollow spikes 16 (on one arm or both arms, opposite or offset) that is connected to the arrangement of the air inlet 14 and air outlet 15 can also be geared to a desired flow profile through the container. Furthermore, the flow can be influenced by the shape of the openings in the hollow spike 16 and of an edge contour of said openings (sharp-edged, rounded, etc.).

Advantageously, the reset device can be simultaneously designed as the joint, as is the case, for example, by means of an arm spring 13, 13' (cf. FIG. 1), as in a clothespin, or by means of the plastics film joint 13 which is shown in FIGS. 4, 6, 8, 10 and 12 and which elastically connects the arms 11, 12.

However, it is not out of the question to also provide a reset device 13' separate from a simple joint 13, as shown in FIG. 2 with a coil spring arranged between the actuation ends 11", 12" and in FIG. 3 with an elastic strap arranged around the action ends 11', 12'.

The action ends 11', 12' of an inhalation device 1 according to the invention comprise hollow spikes 16 which protrude into the recess 17 and are assigned to the air inlet 14 and air outlet 15 (except for a variant shown in FIG. 8, in which only one hollow spike 16' assigned to the air outlet protrudes into the recess 17, though a bypass line 14" is integrated as air inlet).

The recess 17 can be formed on one or both action ends 11', 12' and, depending on the design of the side walls 110, 120 and also of the ceiling 111 and of the floor 121, be formed as a chamber with virtually closed walls or else just as a slot with lateral boundary and contact surface. The chamber or the contact surface can be preshaped in a manner appropriate for a predetermined container shape, for example capsule, cartridge or blister, in order to facilitate insertion for the user.

Using an inhalation device according to the invention, it is possible to open capsules, blisters and special vessels having perforable regions. A powder container which can be used with the inhalation device according to the invention can also contain a freely movable disagglomerator, which is swirled around in the inspiration-based air stream and ensures improved disagglomeration and dispersion of the powder.

As can be seen in the examples from FIGS. 1 to 3, an inhalation device according to the invention can comprise multiple pieces and consist of the two arms 11, 12, the joint 13 and optionally the separate reset device 13'. The hollow spikes 16 can be produced integrally with the arms 11, 12; however, it is also conceivable that they, for example, are present as insert in the injection-molded arm or have been integrated retrospectively. Whereas the arms are preferably cost-effectively made of plastic, the hollow spikes—when they are not integrally injection-molded with the arms—can also be composed of another material, which can, for example, be metal, but also another (harder) plastic.

However, as can be seen in FIGS. 4, 6, 8, 10, 12, an inhalation device according to the invention can preferably be of a one-piece design as a pliers-like clamping device which perforates the container containing the inhalable substance by means of hollow spikes when the action ends are brought together by the reset force or closing force.

FIGS. 4*a*) to *e*) show an inhalation device 1 according to the invention in various views. Said inhalation device 1 is of a one-piece design and is preferably produced in a plastics injection-molding process. Both arms 11, 12 are joined to one another in an articulated manner via a type of film hinge 13, which is formed such that the arms 11, 12 are pretensioned such that the action ends 11', 12' are closed. On the upper arm 11, a mouthpiece is formed on the action end 11' as air outlet 15, which mouthpiece is connected to the air outlet line 15', which line stretches through the hollow spike 16, which spike is arranged on the upper arm 11 with protrusion into the recess 17. The hollow spike 16 for the air feed line 14' on the lower arm 12 protrudes into the recess 17 in an axially offset manner, as can be seen in FIGS. 4*b*)

to *d*). In the present example, there are three air feed lines 14' and three air outlet lines 15', which each stretch from the air inlet or air outlet 14, 15 to the respective hollow spike 16. A distinct notch 18' is provided around the air inlet 14 in order to prevent, for instance, an unintended closure of the air inlet 14 by a finger.

The recess 17 on the action ends 11', 12' of the arms 11, 12 is delimited by the side walls 110 and 120 and also the ceiling 111 and the floor 121. However, both the ceiling 111 and the floor 121 have a window 18 opposite the respective hollow spike 16, and so it is possible to check from the outside whether a container is correctly inserted in order to be penetrated by both hollow spikes 16. Sufficient stability of the lower arm 12 is ensured by bars 122, which stretch from the outwardly curved section of the action end 12' up to alongside the window 18.

In the present example, the hollow spikes 16 are pyramid-shaped with a triangular base area, as can be especially seen in FIGS. 4 *c*) and *d*). The three edges of the pyramid are designed to be sharp-edged, as cutting edges; to this end, the side areas can optionally be grooved. Situated on each side area of the pyramid is an opening, each one communicating with the air feed line or air outlet line 14', 15'.

For the insertion of a container containing an active-ingredient-containing powder or an aroma preparation as inhalable substance, for example in the form of a blister 2, as sketched in FIG. 5, which can consist of a bowl element 20 sealed by a film element 21 on the protruding edge 22, the actuation ends 11", 12" of the inhalation device 1 are pressed together, and so the action ends 11', 12' open. The blister 2 can then be inserted into the recess 17 in order to be penetrated by the hollow spikes 16 upon closure of the action ends 11', 12' when the force exerted on the actuation ends 11", 12" is reduced. When the action ends 11', 12' are closed, the edge 22 of the blister 2 can be clamped between the side walls 110, 120 and the hollow spikes 16 protrude into the interior of the blister 2.

In the case of the hollow spikes with cutting edges, the wall of the blister is cut and bent open without splinter formation. Since the openings to the air feed and air outlet lines 14', 15' are in a groove, an air stream can pass the bent-open wall pieces unhindered.

In the further FIGS. 6, 8, 10, 12, the features corresponding to the exemplary embodiment from FIG. 4 are only partly provided with reference signs, since the explanations essentially do not differ or only insignificantly differ except for the design of the recess 17 for accommodating different containers and of the arrangement of the hollow spikes 16, and so the explanations given for example in connection with FIG. 4 also apply to the further examples.

The inhalation device in FIGS. 6*a*) and *b*) therefore differs from the example depicted in FIG. 4 only in that the recess 17 has a round cross section, and is thus optimized for accommodating a cylindrical container such as a capsule 2 (cf. FIG. 7) consisting of two bowl elements 20 connected to one another at an overlap 20'.

What are described here in relation to FIGS. 4, 6, 8, 10, 12 are inhalation devices 1, the recesses 17 of which are optimized for certain containers 2; however, this is not intended to restrict the inventive subject matter to the extent that said subject matter can only be used with certain containers. For instance, the capsule 2 from FIG. 5 can absolutely also be used in the inhalation device 1 from FIG. 4 that is optimized for a blister—precisely for this purpose, the windows 18, by means of which the position of the container can be checked, are useful.

FIG. 10 shows an inhalation device 1 in which both the air inlet 14 and the air outlet 15 are arranged on the upper arm 11. Accordingly, the hollow spikes 16 are also only arranged on the upper arm 11 with protrusion into the recess 17, whereas the action end 12' of the lower arm 12 is formed with side walls 120 without a floor. Inwardly, the side walls 120 have contact surfaces which can be shaped in a manner appropriate for a container 2 which is intended to be accommodated. The action end 11' of the upper arm 11 does not have side walls, but only a ceiling 111 through which the air feed and air outlet lines 14', 15' stretch. Thus, the ceiling 111 of the upper arm 11 forms a "lid" for the recess 17 delimited by the side walls 120. A container 2 which can be used in an inhalation device 1 having the hollow spikes 16 on one arm 11 is shown in FIG. 11 with a rectangular-shaped special container 2. In line with the arrangement of the hollow spikes 16, said container 2 has two predetermined opening sites 21' for the air inlet and air outlet. Said opening sites 21' in the wall 23 of the container 2 are overmolded with a plastics layer, preferably an elastomer layer (as "sealing disk" or sealing ring). Alternatively, instead of an opening, it is also possible to provide a thin spot in the wall 23 at the opening sites 21'. The advantages of this embodiment are the tightness of the opening sites 21' designed with thinner wall thickness, even after withdrawal of the hollow spikes 16, and also the absence of splinters upon opening, and the guidance of the hollow spikes 16 that is enabled by the elastomer layer.

A special container of this kind need not be rectangular-shaped; it can also be shaped differently, for example rounded. For example, it is conceivable to also insert capsule-shaped containers in the inhalation device from FIG. 10, which containers can then rest on the rounded contact surface of the on the side wall.

FIGS. 12 and 13 illustrate some details or alternative embodiments of an inhalation device 1 according to the invention, which, like the example from FIG. 10, has air inlet and air outlet 14, 15 on the same arm 11 and is likewise produced as one piece in an injection-molding process. However, in comparison with FIG. 10, the action ends 11', 12' are shorter and the hollow spikes 16 for air inlet and air outlet 14, 15 are closer together, and so it is possible to insert a shorter container 2, the edge 22 of which protrudes from the inhalation device 1, the bowl element 20 being sealed by the film element 21 on said edge 22. As a consequence of the shortened action ends 11', 12', the mouthpiece-shaped air outlet 15 stretches up to the bulge of the arm 11 in the region of the joint 13. FIG. 13 illustrates especially the arrangement of the blister-type container 2 between the arms 11, 12. As can also be seen in FIG. 12, the edge 22 protrudes forward out of the inhalation device and is additionally clamped between the side walls 110 and 120.

In FIG. 12, it can be seen that the actuation ends 11", 12" are provided with a surface structure 19 on the sides facing away from one another, in order to facilitate actuation for the user and to allow a safe grip without slipping. Such a surface structure 19 can, for example, be a surface with ribs or a surface with bumps.

The inhalation device 1 from FIG. 8 is designed as "aroma inhaler" or vaporizer for the inhalation of a vaporizing or vaporizable active ingredient or aromatic substance with only one hollow spike 16' having an air outlet line 15' to the air outlet 15. Said inhalation device 1 can, but need not, have an air inlet or a bypass air supply line 14" (depicted in dotted line in FIG. 8*b*); this is because the negative pressure generated in an inserted container (see blister 2 from FIG. 9) upon inhalation assists/promotes the vaporization of the preparation present. However, if the negative pressure generated in the container by the sucking-in of air during inhalation becomes too great, the user can put down the inhalation device 1 and air can subsequently flow through the air outlet into the container, and so it is possible to inhale again. However, in order to prevent a negative pressure generated in the container upon inhalation from becoming too great, it is preferably possible to provide a bypass supply line 14" so that, during inhalation, air can subsequently flow into the container through the bypass supply line 14". An aroma preparation can comprise a carrier substance to regulate vaporization. Unlike in FIGS. 4 and 6, the recess 17 is not designed here to be a type of chamber; at the action end 12', the lower arm 12 has side walls 120 with shaped contact surfaces, but no floor. The action end 11' of the upper arm 11 consists virtually only of the ceiling 111, which forms a "lid" in relation to the side walls 120 of the lower arm 12. Optionally, what can also be envisaged here is that the edge 22 of the blister 2 is clamped between the ceiling 111 and the side walls 120.

The active ingredients and aromatic substances inhalable using the inhalation device according to the invention can be present both as a powder and as a vaporizing or vaporizable solid (pasty) or liquid preparation and comprise not only the aromatic substances (e.g., essential oils), but also all medicaments known for inhalation for the treatment of respiratory diseases and pain, including migraine, and mental impairments such as tension or depressions and also for vaccination and for insulin therapy.

Thus, an inhalation device according to the invention can be used not only with powder containers, enabling the inhalation of an active-ingredient-containing powder as an aerosol, but also with containers containing a vaporizable active-ingredient preparation or aroma preparation, meaning that a vapor containing very fine droplets instead of particles is inhaled.

Devices called vaporizers for vaporizing active ingredients are known. Unlike in the case of vapor inhalers, what is directly vaporized here is not a solution but the substance, optionally in a preparation containing a carrier substance. The active-ingredient preparation or aroma preparation can be present in liquid form or solid or pasty form.

By means of vaporization, it is possible to inhale not only tobacco ("electronic cigarette"), but also pharmaceutical drugs such as cannabis or else plants, or plant parts or extracts. Examples of plants having a sedative action are valerian (*Valeriana officinalis*) as sedative and against spasmodic complaints in the gastrointestinal tract, hop (*Humulus lupulus*) as mild sleep-inducing agent and sedative; St. John's wort (*Hypericum perforatum*) is used for the treatment of mild to moderate depressive moods or nervous restlessness, lavender (*Lavandula angustifolia*) is used as sedative in restless states and in difficulties with falling asleep, but also in nervous complaints concerning the gastrointestinal tract and gall bladder, and maypop (*Passiflora incarnata*) is used against nervous restless states, as sleep-inducing aid or else as anxiolytic and antispasmodic agent. Lemon balm (*Melissa officinalis*) too acts as sedative and digestion promoter.

Further examples of plants containing medicinal active ingredients are damiana (*Turnera diffusa*), a natural aphrodisiac and usable against colds, infectious diseases or blood vessel disorders and as tonic, bluegum (*Eucalyptus globulus*), which is used in colds and asthma because of its expectorant, mildly antispasmodic and antibacterial action, Iceland moss (*Cetraria islandica*) against mucosa irritations in the mouth and throat, and also in inflammations of the stomach mucosa and intestinal mucosa. Moreover, Iceland moss acts against nausea, increases appetite, is stimulating and is invigorating. Chamomile (*Chamomilla recutita*) is used as anti-inflammatory, for cramp relief, against flatulence and as stomachic. Peppermint (*Menthaxpiperita*) has a stimulatory effect on bile flow and bile production, an antispasmodic effect in gastrointestinal complaints, an antimicrobial effect and an antiviral effect. Furthermore, the essential oil is used against migraine, headaches and nerve pains and also in colds; sage (*Salvia officinalis*) with bacterial, anti-inflammatory and astringent action, indicated in inflammations of the mouth and throat. Yarrow (*Achillea* spp.) is used as tonic in digestive disorders and colics, the essential oils have an expectorant action. Thyme (*Thymus vulgaris*) is used in infections of the upper airways, in bronchitis and whooping cough. Yohimbe (*Pausinystalia yohimbe*) acts as aphrodisiac and impotence remedy.

An intoxicating, euphoric or sedating, hallucinogenic, psychoactive or memory-opening action is had by not only cannabis (*Cannabis sativa*), but also lion's tail (*Leonotis leonurus*, "wild dagga"), ayahuasca, yagé (*Banisteriopsis caapi*), blue lotus (*Nymphaea caerulea*), fly agaric (*Amanita muscaria*), kratom (*Mitragyna speciosa*), sinicuichi (*Heimia salicifolia*), esfand (*Peganum harmala*) and sage of the diviners (*Salvia divinorum*). These plants may also have further ingredients with drug action, for example for pain relief, which can be expediently medically administered by vaporization, since in this way no combustion products are generated.

Vaporizers differ especially with respect to the feeding of the heat of vaporization required for vaporization. What can be heated is thus either the substance to be vaporized or the air that is fed. Usually, the temperature can be adjusted according to the desired vaporization temperature by means of suitable controllers and kept constant. In this connection, the substance is preferably heated only to the extent that the desired ingredients vaporize.

In the case of a vaporizer without feeding of heat of vaporization, an air stream is mixed with the saturated air around the vaporizer. The concentration of the inhalant can be controlled by splitting the supply air stream into the vaporizer chamber and into a bypass branch. However, it should be noted here that the saturation content is dependent on the ambient temperature.

If an inhalation device according to the invention is designed as a vaporizer, it is possible to provide a heating device having at least one heating element in order to directly heat the substance to be vaporized to a desired temperature or to heat the supply air stream to a desired temperature. The heating device can comprise not only the heating element, but also an energy carrier such as an accumulator or a battery.

Lastly, it should be pointed out that the hollow spikes 16, 16' used in the inhalation device according to the invention do not necessarily have to be designed as a pyramid-shaped spike with a triangular base area, as can be seen in the examples in FIGS. 4 and 10. In general, what is also conceivable is the use of sharp-edged, pointed four-edged or five-edged spikes, in which the air feed and air outlet openings are then, however, necessarily smaller. In addition, the cutting edges can be less sharp-edged than in the case of a three-edged object. FIG. 14 shows alternative hollow spike devices 16, 16': in a), a conventional conical hollow spike 16, 16', by means of which the container wall is, however, more pierced than cut through; in b), an arrangement composed of multiple hollow spikes 16, 16', which are arranged here on a common support structure 16" (but can also be made integrally with an inhalation device in an injection-molding process), for assignment to the air outlet 15 or air inlet 14 or the bypass supply air line 14"; and in c), as hollow spike 16, 16', a plate 16" having two openings, which are each bridged by two cutting bars 16'''. Said cutting bars 16''' have inclined cutting edges for cutting through the container wall, and so an air stream can penetrate through the openings into the or out of the container. As in the case of the support structure of the hollow spike arrangement from b), it is also possible here to omit the plate per se in one configuration of the hollow spike arrangement on an inhalation device, and so the openings bridged by the cutting bars 16''' are directly present in the relevant action end.

The hollow spikes can be designed as in EP 1 762 265 A1, the content of which is hereby fully incorporated by reference, and in which one air inlet opening is provided on each side of the pyramid-shaped spike. Preferably, however, it is possible in the case of an inhalation device according to the invention for the air feed openings of a hollow spike 16, 16' to be oriented not exactly symmetrically—i.e., in the case of a tetrahedral spike at an angle of 120°—as can be seen in the top view in FIG. 14*d*). Unevenly distributed air inlet openings especially in conjunction with different diameters of the air inlet openings—the channels of the air feed lines 14' can, for example, become successively smaller or larger—ensure that the sucked-in air is made to move spirally when it enters the container 2, resulting in the powder entrainment being improved.

FIGS. 15 and 16 show a further embodiment of an inhalation device 1 according to the invention, in which there is placed on the air outlet 15 a disagglomeration attachment 30, which is provided with a latticed disagglomeration structure 31. Said disagglomeration structure 31 assists the disagglomeration of the powder particles carried off with the air stream from the container, but also serves as catchment grill for film pieces which may possibly arise during opening of the container. The latticed disagglomeration structure 31 can be planar; preferably, however, and depending on the powder to be inhaled, the latticed disagglomeration structure 31 can be curved in a concave or convex manner. The curvature and the direction thereof influence disagglomeration and deposition. In this connection, the pharmaceutical formulation of the powder determines which shape is more favorable. The disagglomeration attachment 30 can be permanently fastened on the outlet 15; however, it can also be designed to be removable, and so the latticed disagglomeration structure 31 can be easily cleaned. Moreover, a removable disagglomeration attachment can be easily exchanged when a different powder is to be inhaled, for which a different shape of the latticed disagglomeration structure 31 is more favorable.

Furthermore, FIG. 15 shows an alternatively designed container 2, the bowl element 20 of which has a narrowing 24, which, upon arrangement in the inhalation device 1, lies between the spike 16 with the air feed line 14' and the spike 16 with the air outlet line 15'. Owing to said narrowing 24, the air stream through the container is quickened, resulting in powder entrainment and disagglomeration being assisted.

Each inhalation device according to the invention can be provided at least in part with an antiseptic or antibacterial and/or antimicrobial coating. For instance, air inlet, air feed line, hollow spikes and air outlet in particular can be coated in order not to inhale pathogens when using the inhalation device. However, because of the relatively simple application, the entire inhalation device can also be coated. An example of such a coating is Perlazid® from Rilit, Endingen. Alternatively, an antiseptic or antibacterial and/or antimicrobial plastic can be used to produce the inhalation device.

Furthermore, the plastic used to produce an inhalation device according to the invention can contain a marker which can be detected on the finished product in order to thus achieve piracy protection, as offered by Polysecure GmbH, Freiburg and disclosed in, for example, DE 10 2008 060 675 B4, DE 10 2012 017 710 A1, DE 10 2012 005 542 A1 or DE 10 2012 003 519 A1.

LIST OF REFERENCE SIGNS

1 Inhalation device
11, 12 Arm
11', 12' Action end
11", 12" Actuation end
110, 120 Side wall on the action end
111, 121 Ceiling, floor on the action end
122 Bar
13, 13' Joint, reset device
14, 14', 14" Air inlet, air feed line, bypass air supply line
15, 15' Air outlet, air outlet line
16, 16', Hollow spike, hollow spike with integr. bypass air supply line,
16", 16''' support structure, cutting bars
17 Recess for container accommodation
18, 18' Window, notch
19 Surface with ribs
2 Container containing active-ingredient-containing powder or aroma preparation
20, 20' Bowl element, overlap
21, 21' Film element, elastomer layer
22 Sealing edge
23 Shaped vessel
24 Narrowing
30 Disagglomeration attachment
31 Disagglomeration structure, lattice

What is claimed is:

1. An inhalation device (1) comprising an air inlet (14), an air outlet (15) designed as a mouthpiece or nosepiece, and a recess (17) designed to accommodate a container (2) containing an inhalable substance, an air channel (L) stretching from the air inlet (14) to the air outlet (15) through the recess (17) and the inhalation device (1) having at least one hollow spike (16, 16') which protrudes into the recess (17) and from which at least one air feed line (14', 14") stretches to the air inlet (14) or at least one air outlet line (15') stretches to the air outlet (15), wherein the inhalation device (1) comprises two arms (11, 12) having in each case an action end (11', 12') and an actuation end (11", 12"), the arms (11, 12) are joined by a joint (13) positioned between the action ends (11', 12') and the actuation ends (11", 12"), the recess (17) is defined between the mutually facing sides of the two arms (11, 12) at the action ends (11', 12'), the at least one hollow spike (16, 16') is arranged inside the recess (17) on one of the mutually facing sides of the two arms (11, 12), and the air inlet (14) and the air outlet (15) are arranged at the action end (11', 12') on a side of at least one of the arms (11, 12), said side facing away from the recess (17), and it being possible for the action ends (11', 12') to be opened or closed by actuation of the arms (11, 12) at the actuation ends (11", 12"), the joint (13) being designed such that an open position (a) of the action ends (11', 12') is provided upon the actuation ends (11", 12") being brought together.

2. The inhalation device (1) as claimed in claim 1, wherein a reset device (13') is in operative connection with the two arms (11, 12) in order to provide a closed position of the action ends (11', 12').

3. The inhalation device (1) as claimed in claim 2, wherein the joint (13) comprises the reset device (13') and is designed as an arm spring or as a film-hinge-type joint (13), or the reset device (13') is an elastic strap arranged around the action ends (11', 12') or is a spring (13'), arranged between the actuation ends (11", 12").

4. The inhalation device (1) as claimed in claim 3, wherein the spring (13') is a coil spring.

5. The inhalation device (1) as claimed in claim 1, wherein the inhalation device (1)

comprises a single hollow spike (16') having an integrated bypass air supply line (14"), or comprises at least two hollow spikes (16), of which at least one is assigned to the air inlet (14) via the at least one air feed line (14') and at least one is assigned to the air outlet (15) via the at least one air outlet line (15'), the at least two hollow spikes (16) both being arranged on one of the arms (11, 12) or at least one of the at least two hollow spikes (16) being arranged on each arm (11, 12), and the hollow spikes (16) being arranged opposite one another or offset with respect to one another.

6. The inhalation device (1) as claimed in claim 1, wherein the inhalation device (1) is made at least partially from plastic.

7. The inhalation device (1) as claimed in claim 6, wherein the inhalation device (1) is made from plastic except for the at least one hollow spike (16, 16').

8. The inhalation device (1) as claimed in claim 6, wherein the inhalation device (1) is made from plastic as one piece and entirely.

9. The inhalation device (1) as claimed in claim 8, wherein the inhalation device (1) is made in an injection-molding process.

10. The inhalation device (1) as claimed in claim 1, wherein the at least one hollow spike (16, 16') is pyramid-shaped.

11. The inhalation device (1) as claimed in claim 10, wherein an air feed line (14') is provided on each side of the pyramid-shaped hollow spike (16, 16').

12. The inhalation device (1) as claimed in claim 11, wherein the air feed lines are arranged asymmetrically in relation to the hollow spike (16, 16') and/or have different diameters.

13. The inhalation device (1) as claimed in claim 10, wherein the at least one pyramid-shaped hollow spike (16, 16') has a triangular base area.

14. The inhalation device (1) as claimed in claim 1, further comprising a disagglomeration attachment (30) which is arranged on the air outlet (15) in a detachable or nondetachable manner and has a disagglomeration structure (31) which stretches across the entire cross section of the air outlet (15).

15. The inhalation device (1) as claimed in claim 14, wherein the disagglomeration structure (31) is latticed, the latticed disagglomeration structure (31) being planar or curved, a curvature direction and/or a mesh size being selectable depending on the powder to be inhaled using the inhalation device (1).

16. A method of using an inhalation device (1) as claimed in claim 1, comprising perforating a container (2) containing an inhalable substance and providing the substance for inhalation.

17. An inhalation kit comprising an inhalation device (1) and at least one container (2) containing an inhalable substance, wherein the inhalation device is an inhalation device (1) as claimed in claim 1.

18. The inhalation kit as claimed in claim 17, wherein the container (2) comprises a narrowing (24) which, upon arrangement of the container (2) in the recess (17) of the inhalation device (1), is arranged between the at least one air feed line (14', 14") and the at least one air outlet line (15').

* * * * *